United States Patent
Kondo et al.

(10) Patent No.: US 10,596,331 B2
(45) Date of Patent: Mar. 24, 2020

(54) PHARMACEUTICAL INJECTING DEVICE, DISPLAY CONTROL METHOD FOR PHARMACEUTICAL INJECTING DEVICE, AND INJECTION SITE DISPLAY DEVICE

(71) Applicant: PHC Holdings Corporation, Minato-ku, Tokyo (JP)

(72) Inventors: Tsuguhiro Kondo, Ehime (JP); Seiji Kikuchi, Ehime (JP); Yasutaka Mukai, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 782 days.

(21) Appl. No.: 15/119,705

(22) PCT Filed: Mar. 23, 2015

(86) PCT No.: PCT/JP2015/058747
§ 371 (c)(1),
(2) Date: Aug. 17, 2016

(87) PCT Pub. No.: WO2015/151900
PCT Pub. Date: Oct. 8, 2015

(65) Prior Publication Data
US 2017/0056605 A1 Mar. 2, 2017

(30) Foreign Application Priority Data
Apr. 1, 2014 (JP) .................. 2014-075597

(51) Int. Cl.
*A61M 5/42* (2006.01)
*G16H 40/63* (2018.01)
(Continued)

(52) U.S. Cl.
CPC ......... *A61M 5/427* (2013.01); *G06F 19/3468* (2013.01); *G16H 40/63* (2018.01);
(Continued)

(58) Field of Classification Search
CPC .................. A61M 5/427; A61M 5/20; A61M 2005/2414; A61M 2205/50;
(Continued)

(56) References Cited

U.S. PATENT DOCUMENTS

| 8,113,845 B2 | 2/2012 | Koster |
| 2007/0197968 A1 | 8/2007 | Pongpairochana et al. |

(Continued)

FOREIGN PATENT DOCUMENTS

| FR | 2980977 A1 | 4/2013 |
| JP | 2010-534552 A | 11/2010 |

(Continued)

OTHER PUBLICATIONS

The Search Report from the corresponding European Patent Application No. 15773432.8 dated Mar. 28, 2017.

(Continued)

*Primary Examiner* — Bhisma Mehta
*Assistant Examiner* — Hamza A Darb
(74) *Attorney, Agent, or Firm* — Wenderoth, Lind & Ponack, L.L.P.

(57) ABSTRACT

A pharmaceutical injecting device comprises a main body case, a piston, a drive mechanism, a display component, and a controller. The body case has a cartridge holder in which a pharmaceutical syringe is installed. The piston is provided movably with respect to the pharmaceutical syringe that is installed in the cartridge holder. The drive mechanism drives the piston. The controller is electrically connected to the drive mechanism. The display component is connected to the controller. The controller has a display controller. The display controller causes the display component to display a plurality of injection sites and to display at two or more injection sites selectable displays indicating that those injection sites are suitable for injection.

18 Claims, 11 Drawing Sheets

(51) Int. Cl.
*G06F 19/00* (2018.01)
*G16H 20/17* (2018.01)
*A61M 5/31* (2006.01)
*A61M 5/24* (2006.01)
*A61M 5/20* (2006.01)

(52) U.S. Cl.
CPC ....... *A61M 5/20* (2013.01); *A61M 2005/2414* (2013.01); *A61M 2005/3125* (2013.01); *A61M 2205/50* (2013.01); *A61M 2205/502* (2013.01); *G16H 20/17* (2018.01)

(58) Field of Classification Search
CPC .... A61M 2205/502; A61M 2205/3125; A61M 5/42; A61M 2005/3126; A61M 2205/505; A61M 2205/507; G16H 40/63; G16H 20/17
See application file for complete search history.

(56) References Cited

U.S. PATENT DOCUMENTS

| | | |
|---|---|---|
| 2009/0030366 A1 | 1/2009 | Hochman |
| 2009/0177154 A1 | 7/2009 | Blomquist |
| 2010/0160857 A1 | 6/2010 | Pongpairochana et al. |
| 2011/0009812 A1 | 1/2011 | Brown |
| 2011/0201998 A1 | 8/2011 | Pongpairochana et al. |
| 2012/0306881 A1 | 12/2012 | Nemoto |
| 2014/0121636 A1 | 5/2014 | Boyden et al. |
| 2014/0121637 A1 | 5/2014 | Boyden et al. |
| 2014/0228763 A1 | 8/2014 | Kondoh et al. |
| 2015/0126963 A1* | 5/2015 | Despa ................ G06F 19/3456 604/506 |
| 2017/0028141 A1 | 2/2017 | Fiedler et al. |

FOREIGN PATENT DOCUMENTS

| | | |
|---|---|---|
| JP | 3171571 U | 11/2011 |
| JP | 2012-050847 A | 3/2012 |
| JP | 3184481 U | 6/2013 |
| WO | 2009/018120 A2 | 2/2009 |
| WO | 2009/018120 A3 | 2/2009 |
| WO | 2012/105577 A1 | 8/2012 |
| WO | 2013/038639 A1 | 3/2013 |
| WO | WO2014/070644 A1 | 5/2014 |
| WO | WO2015/066522 A1 | 5/2015 |
| WO | WO2015/085019 A1 | 6/2015 |
| WO | WO2015/136564 A1 | 9/2015 |

OTHER PUBLICATIONS

The Notice of Allowance from the corresponding Japanese Patent Application No. 2016-511552 dated Mar. 6, 2018.
Internationanl Search Report of corresponding PCT Application No. PCT/JP2015/058747 dated Jun. 16, 2015.

* cited by examiner (a)  (b)

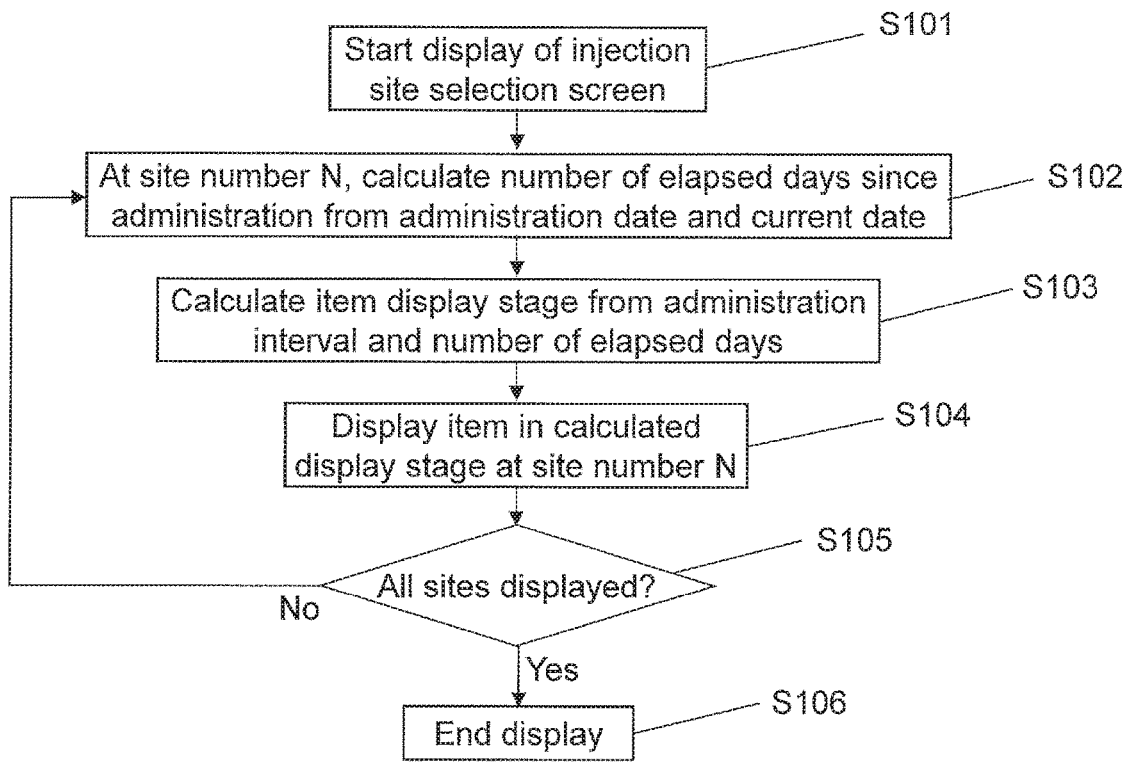

FIG. 12

| Site No. | Name | Administration interval | Administration date | Item |
|---|---|---|---|---|
| 1 | right abdomen | 5 | xx/xx/xxxx | apple |
| 2 | left abdomen | 5 | xx/xx/xxxx | watermelon |
| 3 | upper right thigh | 5 | xx/xx/xxxx | cherry |
| 4 | upper left thigh | 5 | xx/xx/xxxx | orange |
| 5 | lower right thigh | 5 | xx/xx/xxxx | grape |
| 6 | lower left thigh | 5 | xx/xx/xxxx | strawberry |
| 7 | upper left arm | 5 | xx/xx/xxxx | banana |
| 8 | upper right arm | 5 | xx/xx/xxxx | pineapple |
| 9 | left buttock | 3 | xx/xx/xxxx | melon |
| 10 | right buttock | 3 | xx/xx/xxxx | peach |

(a)　　　　　　　　　(b)

(a)　　　　　　　　　(b)

| History No. | Administration date | Dose | Site No. | Name | Administration interval record | Item |
|---|---|---|---|---|---|---|
| 1 | xx/xx/xxxx | 1.0 mg | 4 | upper left thigh | 100 | orange |
| 2 | xx/xx/xxxx | 1.0 mg | 1 | right abdomen | 100 | apple |
| 3 | xx/xx/xxxx | 1.0 mg | 9 | left buttock | 100 | melon |
| 4 | xx/xx/xxxx | 1.0 mg | 8 | upper right arm | 100 | pineapple |
| 5 | xx/xx/xxxx | 1.0 mg | 5 | lower right thigh | 100 | grape |
| 6 | xx/xx/xxxx | 1.0 mg | 2 | left abdomen | 100 | watermelon |
| 7 | xx/xx/xxxx | 1.0 mg | 10 | right buttock | 100 | peach |
| 8 | xx/xx/xxxx | 1.0 mg | 7 | upper left arm | 100 | banana |
| 9 | xx/xx/xxxx | 1.0 mg | 1 | right abdomen | 7 | orange |
| 10 | xx/xx/xxxx | 1.0 mg | 3 | upper right thigh | 100 | cherry |
| 11 | xx/xx/xxxx | 1.0 mg | 2 | left abdomen | 5 | pineapple |
| 12 | xx/xx/xxxx | 1.0 mg | 6 | lower left thigh | 100 | strawberry |
| 13 | xx/xx/xxxx | 1.0 mg | 4 | upper left thigh | 12 | apple |
| 14 | xx/xx/xxxx | 1.0 mg | 7 | upper left arm | 6 | watermelon |
| 15 | xx/xx/xxxx | 1.0 mg | 5 | lower right thigh | 10 | grape |
| | | | | | | |
| 365 | xx/xx/xxxx | 1.0 mg | 5 | lower right thigh | 8 | melon |

FIG. 19

PHARMACEUTICAL INJECTING DEVICE, DISPLAY CONTROL METHOD FOR PHARMACEUTICAL INJECTING DEVICE, AND INJECTION SITE DISPLAY DEVICE

PRIORITY

This is a National Stage application under 35 U.S.C. § 365 of International Application PCT/JP2015/058747, with an international filing date of Mar. 23, 2015, which claims priority to Japanese Patent Application No. 2014-075597 filed on Apr. 1, 2014. The entire disclosures of International Application PCT/JP2015/058747 and Japanese Patent Application No. 2014-075597 are hereby incorporated herein by reference.

TECHNICAL FIELD

Certain implementations of the present invention relate to a pharmaceutical injecting device for injecting insulin, growth hormone, or another such pharmaceutical, to a display control method for a pharmaceutical injecting device, and to an injection site display device.

BACKGROUND

A conventional pharmaceutical injecting device of this type was configured as follows.

Specifically, the configuration comprised a main body case having a pharmaceutical syringe installation component, a piston provided movably with respect to the pharmaceutical syringe installed in this pharmaceutical syringe installation component, drive mechanism that drives this piston, a controller that is electrically connected to this drive mechanism, and a display component that is connected to this controller.

SUMMARY

In the above-mentioned conventional example, the patient himself injects a pharmaceutical into his own body by his own operation. This is often used, for example, for injecting growth hormone into a child. The growth hormone is injected every other day, for example, but if it is always injected at the same site, that site can undergo an injection site reaction that causes redness, swelling, and itching.

However, particularly in the case of a child, the patient often ends up always injecting at a site that is easy for him to inject. Consequently, continuous injection at the same site ends up causing problems.

In view of this, it is an object of certain implementations of the present invention to provide a pharmaceutical injecting device, a display control method for a pharmaceutical injecting device, and an injection site display device, with which problems are less likely to be caused by continuous injection at the same site.

To achieve this object, certain implementations of the present invention comprise a main body case, a piston, a drive mechanism, a display component, and a display controller. The main body case has a pharmaceutical syringe installation component in which a pharmaceutical syringe is installed. The piston is provided movably with respect to the pharmaceutical syringe installed in the pharmaceutical syringe installation component. The drive mechanism drives the piston. The display component displays injection sites at which the pharmaceutical in the pharmaceutical syringe is injected. The display controller causes the display component to display a plurality of the injection sites and to display at two or more injection sites selectable displays indicating that those injection sites are suitable for injection. This achieves the stated object.

As discussed above, the display controller of certain implementations of the present invention causes the display component to display a plurality of the injection sites and to display at two or more injection sites selectable displays indicating that those injection sites are suitable for injection.

Accordingly, since selectable displays are displayed at two or more injection sites, the patient can choose a site each time that affords easy injection from among the injection sites displayed in selectable form. Furthermore, the site the patient chooses will be an injection site that is suitable for injection, that is, one at which continuous injection is unlikely to pose a problem.

Therefore, even if the patient is a child, he can inject at a site where injection is easy for him, and can be guided to inject at a site where continuous injection is unlikely to pose a problem.

As a result, problems caused by continuous injection at the same site are less likely to occur.

BRIEF DESCRIPTION OF THE DRAWINGS

FIG. 11 is a flowchart of the operation of the pharmaceutical injecting device in FIG. 1;

FIG. 12 is a table of information about injection sites for the pharmaceutical injecting device in FIG. 1;

FIG. 19 is a pharmaceutical administration history table pertaining to a modification example of an embodiment of the present invention.

DETAILED DESCRIPTION

Figure 1:
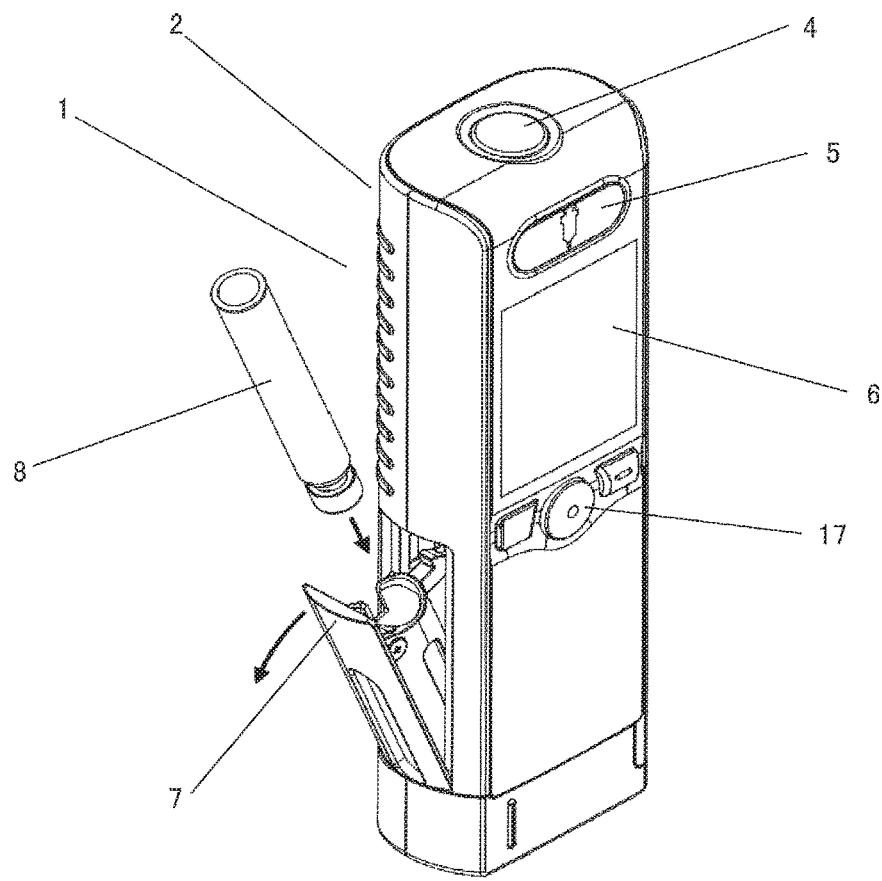
FIG. 1 is an oblique view of the pharmaceutical injecting device pertaining to an embodiment of the present invention.
Figure 2:
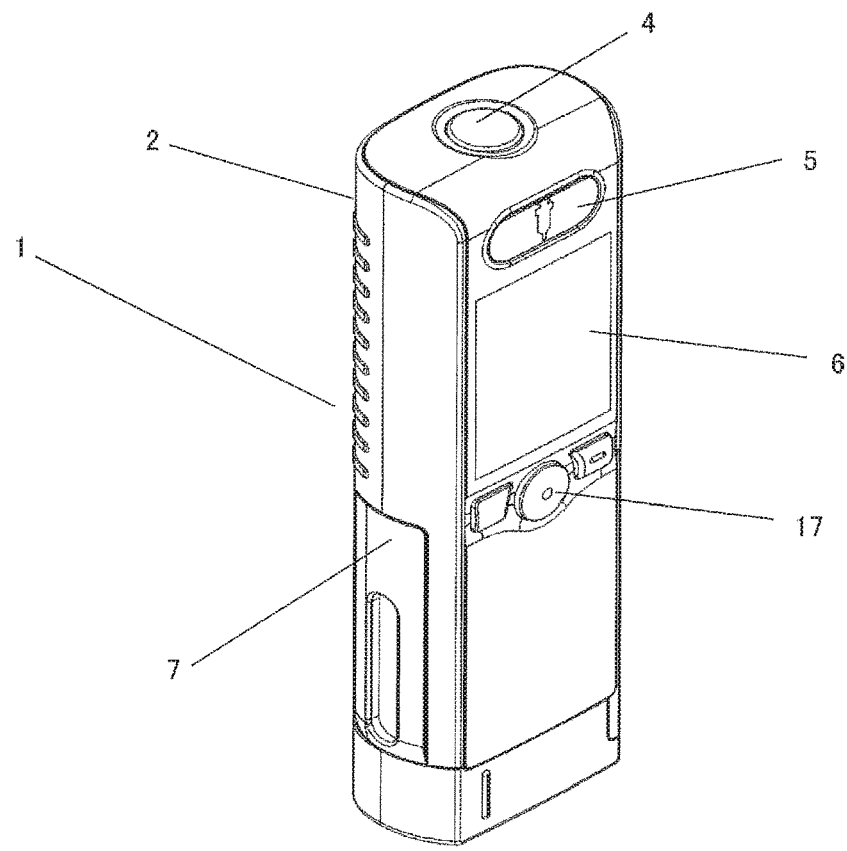
FIG. 2 is an oblique view of the state when the cartridge holder of the pharmaceutical injecting device in FIG. 1 has been closed.
Figure 3:
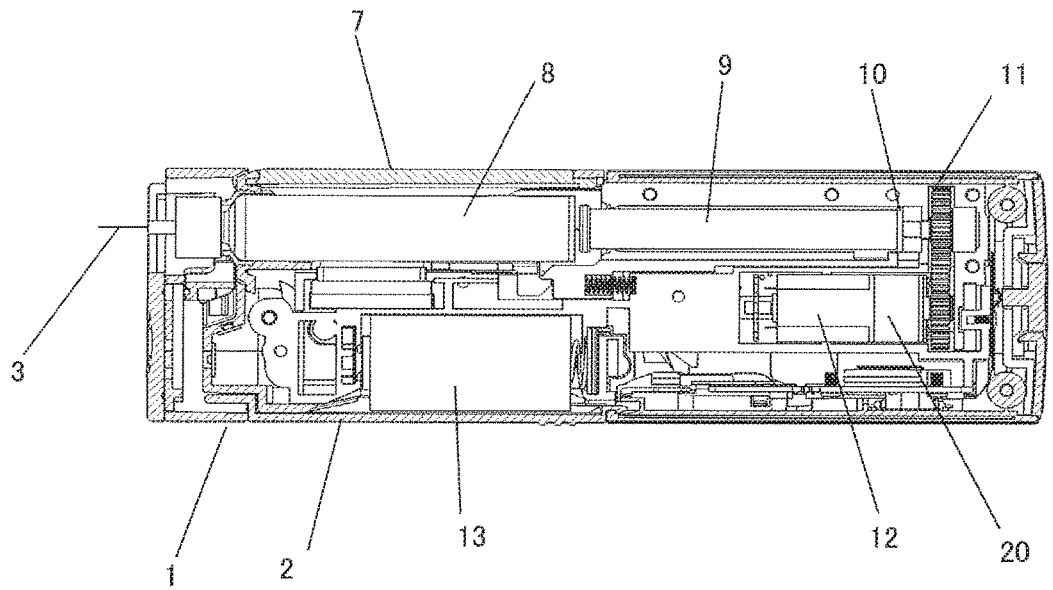
FIG. 3 is a cross section of the pharmaceutical injecting device in FIG. 1.

An embodiment of the present invention will now be described through reference to the appended drawings.
1. Configuration
Overview of Pharmaceutical Injecting Device FIGS. 1 and 2 show the outside of the pharmaceutical injecting device 1 in this embodiment. FIG. 3 shows the internal configuration of the pharmaceutical injecting device 1 in this embodiment.

In this embodiment, the user (patient) uses the pharmaceutical injecting device 1 in FIG. 1 to inject a growth hormone once a day, for example.

As shown in FIGS. 1 to 3, the pharmaceutical injecting device 1 in this embodiment comprises a cylindrical main body case 2. One end (the lower end side) of the main body case 2 is configured so that an injection needle 3 is installed. A power button 4 used to turn on the power to the pharmaceutical injecting device 1 is provided to the other end (the upper end side) of the main body case 2. A pharmaceutical injection button 5 for performing injection and a display component 6 for displaying injection instructions are provided to the front face of the main body case 2 in that order, from the upper end side to the lower end side. The pharmaceutical injection button 5 and the display component 6 are disposed closer to the power button 4.

A cartridge holder 7 is provided at one end (the lower end side) of the main body case 2 so as to be capable of opening and closing as shown in FIGS. 1 and 2. A pharmaceutical syringe 8 is installed in this cartridge holder 7. That is, the cartridge holder 7 serves as a holder in which the pharmaceutical syringe 8 is held.

When it is time to administer (inject) a pharmaceutical, the user puts the pharmaceutical syringe 8 into the cartridge holder 7 as shown in FIG. 1, and closes the cartridge holder 7 as shown in FIG. 2.

In a state in which the pharmaceutical syringe 8 has been installed in the cartridge holder 7, a piston 9 is provided to the rear of the pharmaceutical syringe 8 as shown in FIG. 3. The piston 9 is provided movably with respect to the pharmaceutical syringe 8. The piston 9 is driven by a drive mechanism 20 made up of a piston feed screw 10, a gear 11, and a motor 12.

In a state in which the injection needle 3 is mounted in front of the pharmaceutical syringe 8, and the skin is pierced with this injection needle 3, if the piston 9 is moved forward (toward the lower end side) by the drive mechanism 20, the pharmaceutical inside the pharmaceutical syringe 8 is injected into the body.

FIG. 3 shows a battery 13 that is used to supply power to the various components.
Control Configuration FIG. 4 shows the electrical connection state of the various components.

The motor 12 of the drive mechanism 20 is connected to a controller 14, and this controller 14 is configured to drive the motor 12. The controller 14 and a memory 15 are constituted by electrical circuits.

The above-mentioned power button 4, pharmaceutical injection button 5, display component 6, battery 13, and memory 15 and a clock 16 are electrically connected to the controller 14. Also, an input component 17 used by the patient to perform various operations is electrically connected to the controller 14. The input component 17 is made up of a plurality of input buttons. These input buttons may be mechanical, or the display component 6 may be made compatible with touch input and display input buttons.

Figure 4:
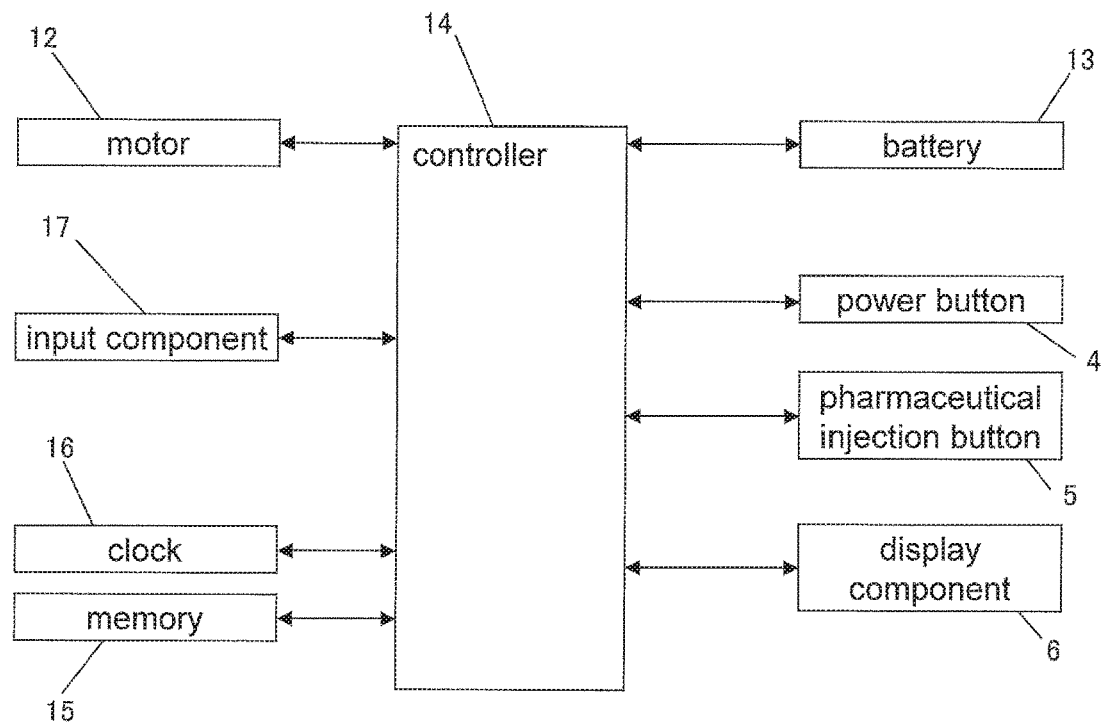
FIG. 4 is a control block diagram of the electrical connection of the pharmaceutical injecting device in FIG. 1.

The controller 14 controls the operation of the various components shown in FIG. 4, and a program that performs this operational control is stored in the memory 15. As will be described in detail below, the controller 14 displays injection site instructions on the display component 6.

The battery 13 is connected only to the controller 14, but is configured to supply power to the various components shown in FIG. 4. The controller 14, the memory 15, and the clock 16 are constituted by electrical circuits, and are provided on a control board (not shown) inside the main body case 2.

The controller 14 also has a display controller 100 (see FIG. 9; discussed below) that controls the display component 6. The display controller 100 causes the display component 6 to give displays related to injection sites, which will be described below. Then controller 14 also has a calculator 101, a determination component 102, and an update component 103, which are related to the display of injection sites. The display controller 100, the calculator 101, the determination component 102, and the update component 103 will be described at a later point.
Display of Injection Sites In the above configuration, the characteristic feature of the pharmaceutical injecting device 1 in this embodiment is that the display component 6 displays a plurality of injection sites, and also displays at two or more injection sites selectable displays indicating that these injection sites are suitable for injection (that is, injection sites where injection is recommended), and the patient himself selects the injection site.

An injection site that is suitable for injection (that is, an injection site where injection is recommended) is one at which problems caused by continuous injection are unlikely to occur if the current injection is made at this injection site. That is, by injecting at this injection site, an injection site reaction that causes redness, swelling, and itching can be prevented.

This will now be described in specific terms.

Figure 5:
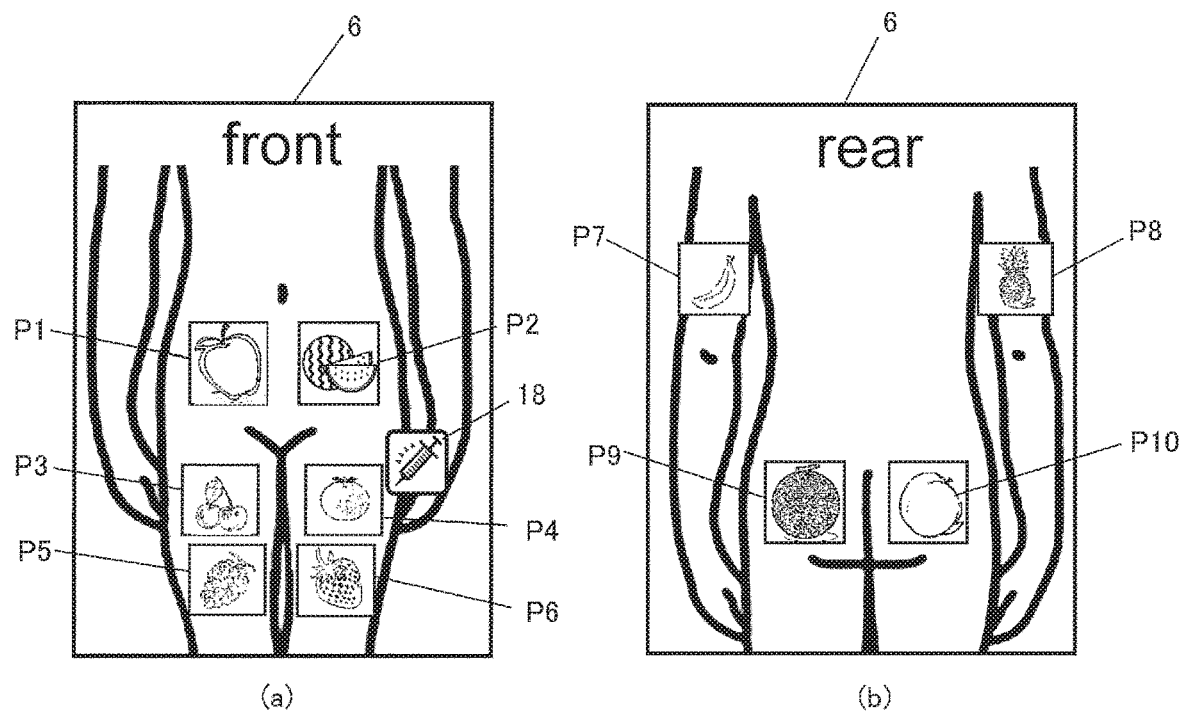
FIGS. 5a and 5b show display examples of the display component in the pharmaceutical injecting device in FIG. 1.

In this embodiment, at the time of an injection, the display controller 100 causes the display component 6 to display a diagram of the human body as shown in FIG. 5, and to display three or more injection sites (here, the ten injection sites P1 to P10) on this human body diagram. The human body diagram is such that the user can switch between the front display in FIG. 5a and the rear display in FIG. 5b by operating the display switch button provided in the input component 17 in FIG. 4.

In this human body diagram, either selectable displays indicating that the sites are suitable for injection (A1 to A10 in FIG. 7; discussed below), or already-selected displays indicating that the sites are not suitable for injection (that is, injection is not recommended) (B1 to B4 in FIG. 8; discussed below) are displayed at the injection sites. The locations of the injection sites are specified by these displays on the human body diagram on the display component 6.

Figure 7:
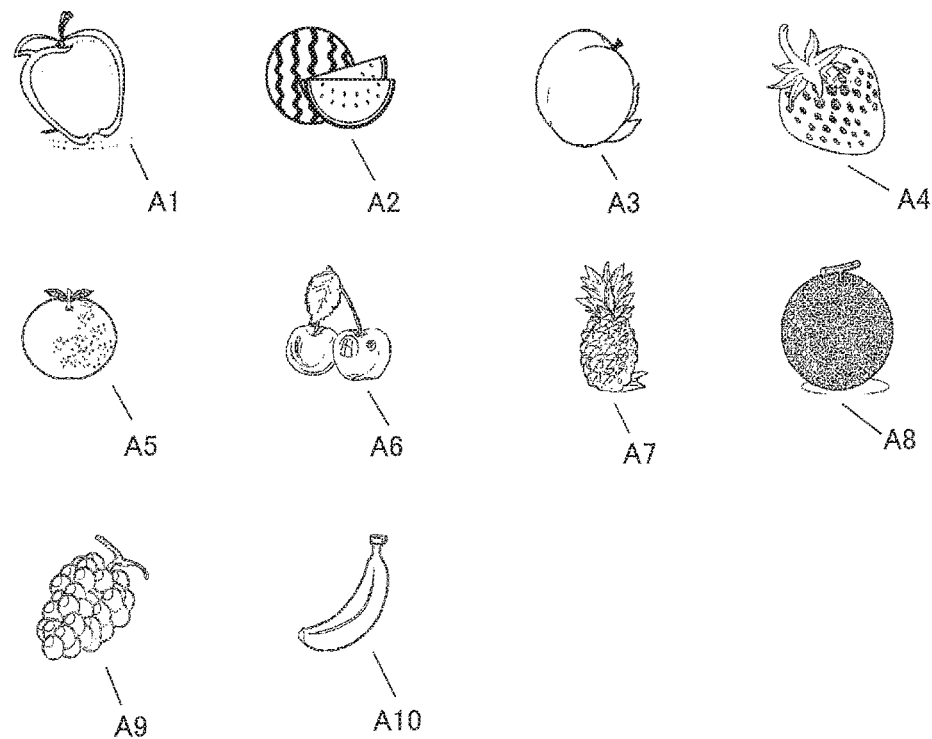
FIG. 7 shows items that are displayed on the display component in the pharmaceutical injecting device in FIG. 1.

The display controller 100 displays the fruits A1 to A10 shown in FIG. 7, as selectable displays, at the injection sites P1 to P10 shown in FIG. 5. That is, the fruits indicate that a site is an injection site that is suitable for injection, and indicate that a site is unlikely to pose problems due to continuous injection.

Specifically, at the time of injection, selectable displays are displayed by fruits at two or more injection sites, so the patient can choose a site at which it is easy for him to inject, from among the injection sites P1 to P10 where the fruits are displayed.

As a result, there are less likely to be problems due to continuous injection at the same site.

The patient chooses, for example, the injection site P4 where an orange is displayed, and makes an injection.

Figure 6:
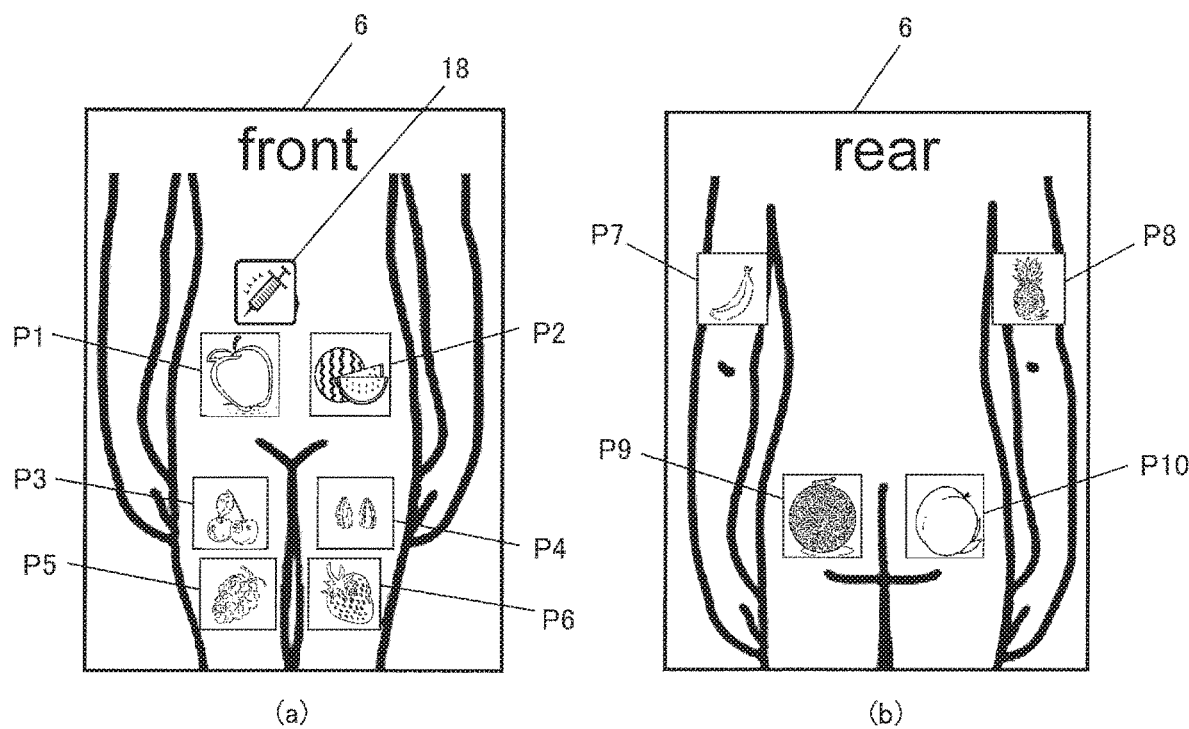
FIGS. 6a and 6b show display examples of the display component in the pharmaceutical injecting device in FIG. 1.

After this, when it is time for an injection the next day, the display at this injection site P4 is changed from an orange to orange seeds as shown in FIG. 6a (already-selected display; see B1 in FIG. 8 discussed below).

Specifically, after injection, the display controller 100 in this embodiment changes the selectable display of one injection site that has been selected to an already-selected display indicating that this site is not suitable for injection (injection is not recommended).

Therefore, the patient can see this already-selected display and recognize that "Today I can't inject at this site," and will therefore not choose the same site twice in a row.

As a result, there are less likely to be problems due to continuous injection at the same site.

Since three or more injection sites are set, even if one of them has already been selected, the patient can select from among the remaining two or more injection sites (that is, a plurality of them).

Also, since the display component 6 displays in color, the various fruits can be recognized more easily.

The display controller 100 in this embodiment gives, as an already-selected display, a display indicating when this selected injection site will next become selectable (a display that estimates the next time).

Figure 8:
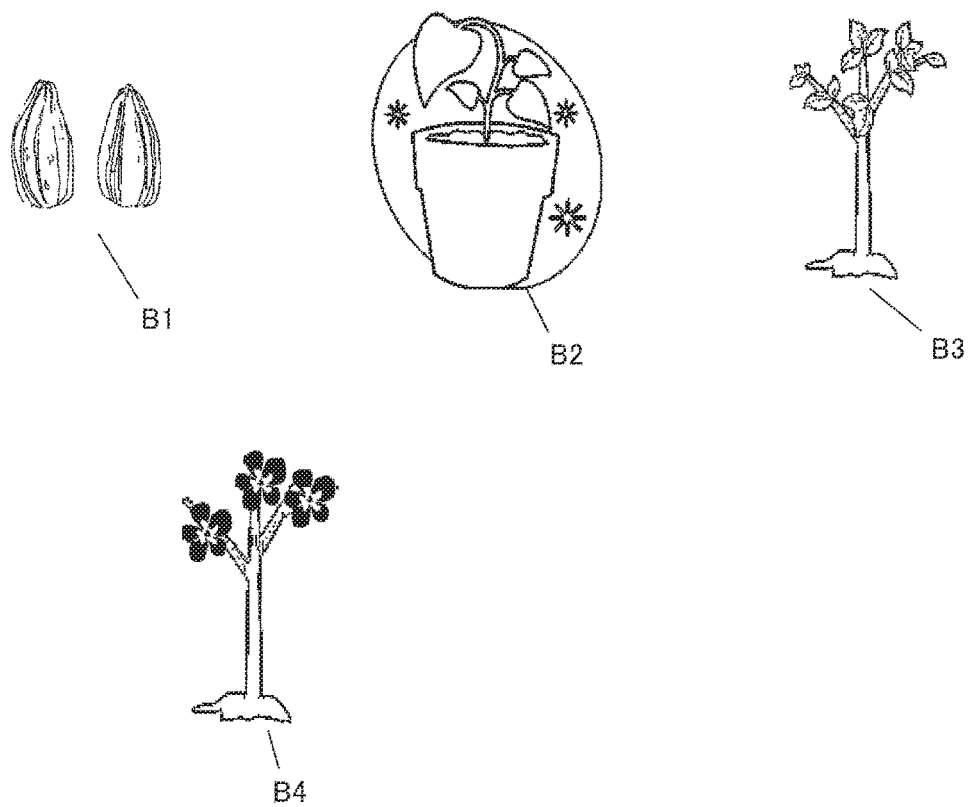
FIG. 8 shows items that are displayed on the display component in the pharmaceutical injecting device in FIG. 1.

More specifically, to indicate when this injection site will next become selectable, the growth state of the fruit displayed at this selected injection site is represented, for instance, in five stages: the seeds in image B1 in FIG. 8, the sprout in image B2, the seedling in image B3, the flowers in image B4, and the mature fruit of the fruits A1 to A10 in FIG. 7. The images B1 to B4 and images of the fruits A1 to A10 are stored in the memory 15.

The images B1 to B4 from seed to flower are used as already-selected displays, and show that the user still cannot inject at those sites. The images for these already-selected displays are readied for all of the fruits A1 to A10, and are stored in the memory 15.

The images of the fruits A1 to A10 are images of the mature fruits in harvest state, and are used for selectable displays. These displays show that their injection site are suitable for injection.

In this embodiment, when the user selects an injection site and makes an injection, the fruit at the injection site that has already been selected is displayed as seeds, indicating a recently planted state. As the days pass since the date when this injection site was selected (also called the administration date or the injection date), the display changes is stages from the seeds of a recently planted state to the fruit in a harvest state.

Therefore, every day after the injection date, the growth state displays goes from seed, to sprout, to seedling, to flowering, to fruit, so the patient can intuitively understand that the day when injection becomes possible is drawing near, and can carry out his daily treatment while enjoying this growth state.

Control Configuration for Displaying Injection Sites

Figure 9:
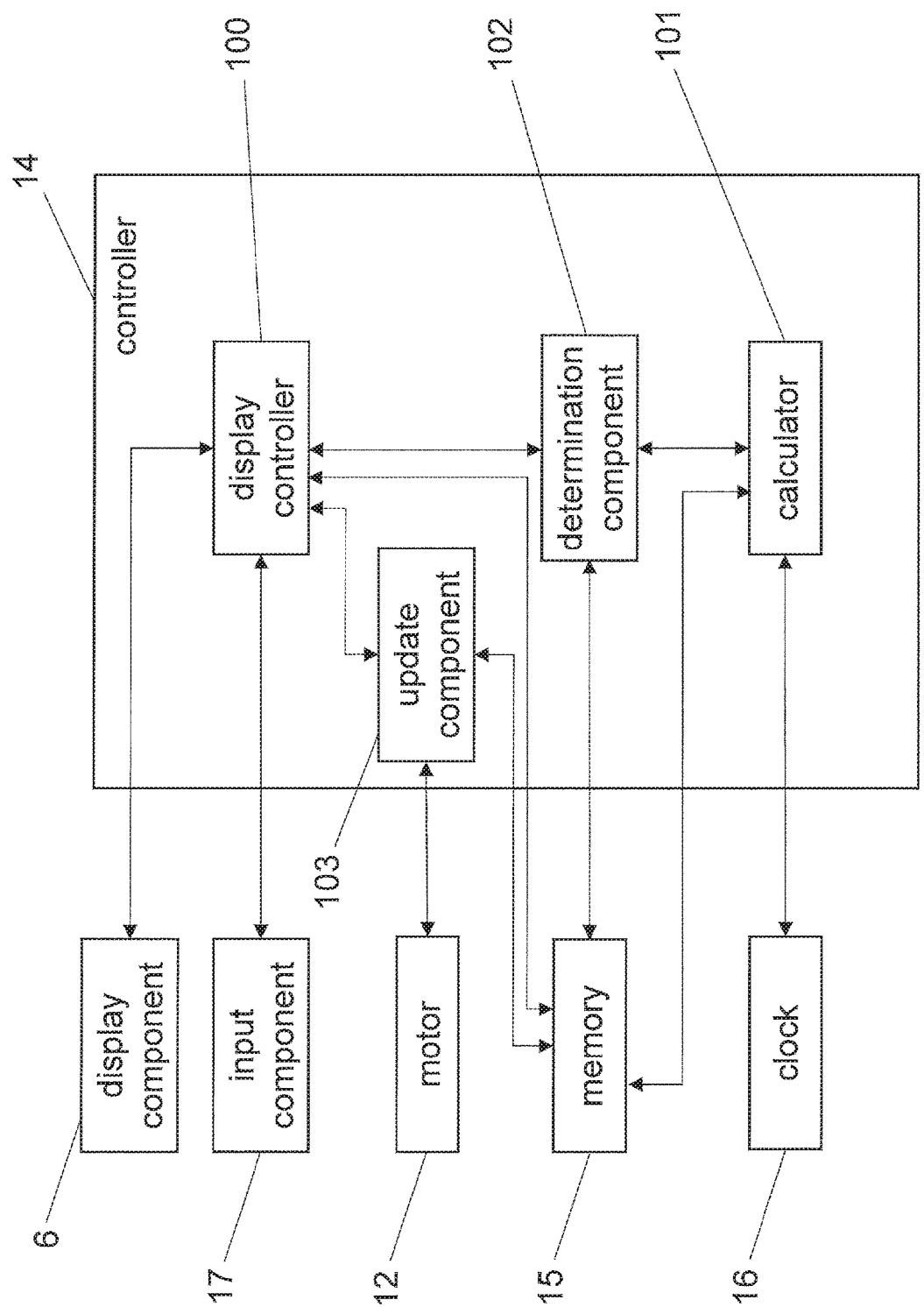
FIG. 9 is a control block diagram related to the control of the display component of the pharmaceutical injecting device in FIG. 1.

FIG. 9 is a control block diagram of the display of injection sites. As shown in the drawing, the controller 14 has the display controller 100, the calculator 101, the determination component 102, and the update component 103.

The display controller 100 controls the display on the display component 6 on the basis of input from the input component 17, information stored in the memory 15, calculations made by the calculator 101, and so forth.

The images A1 to A10 and B1 to B4 shown in FIGS. 7 and 8 and the information table T1 shown in FIG. 12 (discussed below) are stored in the memory 15. The information table T1 will be discussed in detail below, but contains information related to injection sites.

The calculator 101 calculates the number of days that have passed since the administration date at each of the injection sites P1 to P10 from the clock 16 and the data stored in the memory 15. The calculator 101 also calculates the number of days that have passed since the pharmaceutical administration date for a selected injection site when the user selects one of the injection sites P1 to P10 in preparing to make an injection.

The determination component 102 determines whether or not each of the plurality of injection sites is a site suitable for injection. An already-selected display (such as the images B1 to B4) indicating that a site is not suitable for injection is displayed at injection sites determined by the determination component 102 to be unsuitable for injection. A selectable display (such as the images A1 to A10) is displayed at injection sites determined by the determination component 102 to be suitable for injection.

More precisely, the determination component 102 calculates the stage at which to display an item from the number of elapsed days calculated by the calculator 101 and the administration interval set in advance by the doctor, etc., and determines which of the above-mentioned five stages to display, for example. Also, the determination component 102 determines whether or not an injection site is suitable for injection from the administration interval and the number of elapsed days calculated for a selected injection site. If a site is not suitable for injection, the display controller 100 causes the display component 6 to give a warning display.

2. Operation

Figure 10:
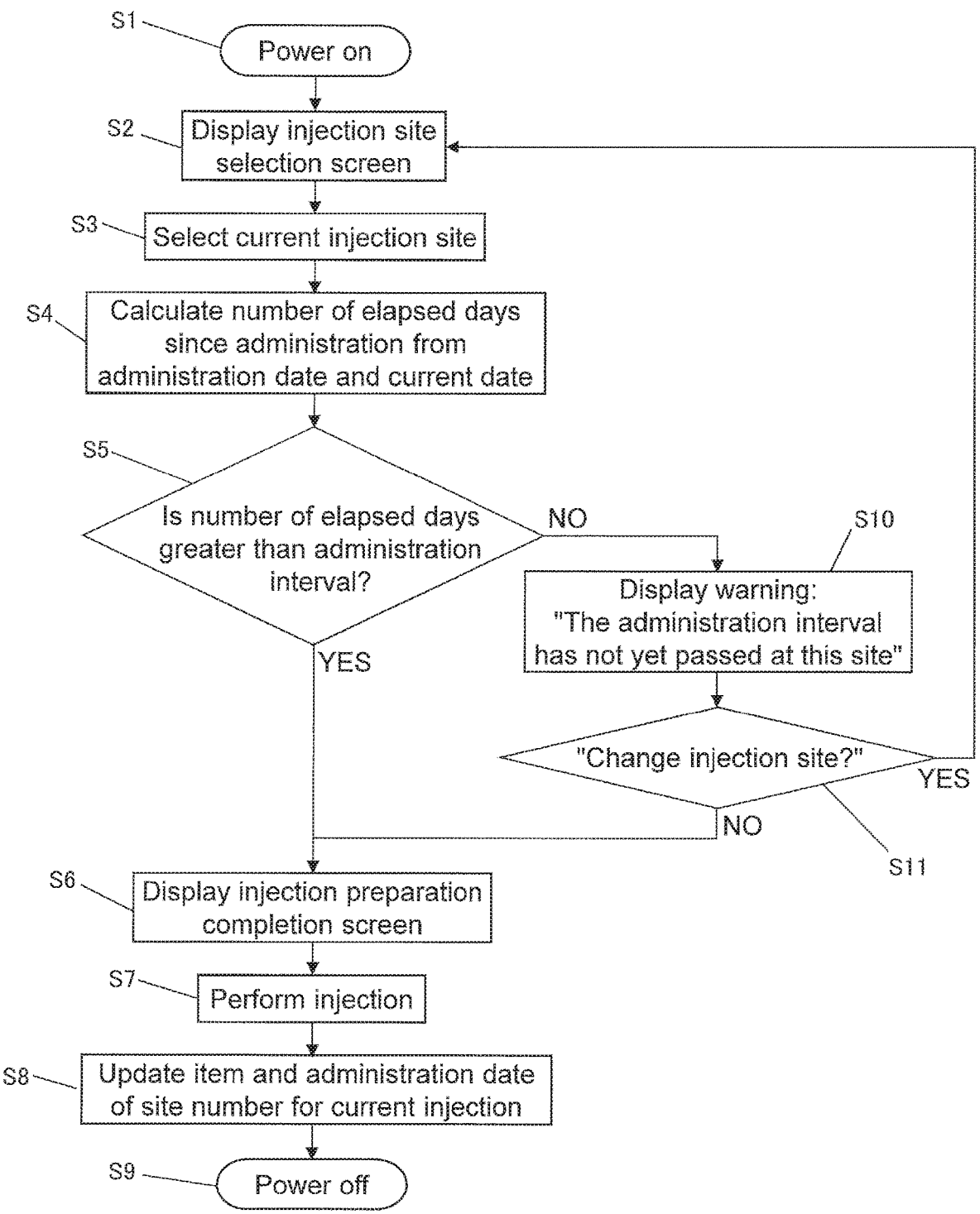
FIG. 10 is a flowchart of the operation of the pharmaceutical injecting device in FIG. 1.

FIGS. 10 and 11 are flowcharts illustrating this display on the display component 6. The program is executed by the components inside the controller 14.

At the time of injection, if the patient operates the power button 4, power is turned on to the pharmaceutical injecting device 1 (S1 in FIG. 10).

In S2 in FIG. 10, the display controller 100 causes the display component 6 to display an injection site selection screen as shown in FIG. 5a. Details of this operation in S2 in FIG. 10 will be described through reference to the operational flowchart in FIG. 11.

Step of Displaying Injection Site Selection Screen

In S101 in FIG. 11, when the display of the injection site selection screen is commenced, the display controller 100 displays the front side of a human body. At this point the processing of S102 to S105 in FIG. 11 is performed on the injection sites P1 to P6, and the growth state of the fruit is displayed.

In S102 in FIG. 11, the display controller 100, the calculator 101, and the determination component 102 read information corresponding to the injection sites P1 to P10 from the information table T1 in FIG. 12. This information table T1 contains the following five types of information related to the injection sites P1 to P10, and is stored in the memory 15.

(1) Site number: Indicates an injection site. Corresponds to injection sites P1 to P10.

(2) Name: Indicates the name of the injection site.

(3) Administration interval: Indicates the interval at which a pharmaceutical is administered. Indicates the number of days until the next injection is possible. Determined so that injection site reaction will be less likely to occur. That is, determined so as to prevent injection site reaction. Varies with injection site. Determined by doctor.

(4) Administration date: Indicates previous pharmaceutical administration date. Also indicates injection date.

(5) Item: Indicates fruit displayed at injection sites P1 to P10. The fruits A1 to A10 in FIG. 7.

For example, information about the injection site P1 includes that the site number is 1, the name is right abdomen, the administration interval is five days, the administration date is not recorded, and the item is an apple.

The number of injection sites and the administration interval are set so that selectable displays will be displayed at two or more injection sites.

The determination component 102 determines whether or not each injection site is a site that is suitable for injection, and the display controller 100 performs either an already-selected display or a selectable display. This will be described in specific terms below.

The calculator 101 calculates the number of elapsed days (that is, how many days it has been since the administration date) from the current date on the clock 16 and the administration date for injection number 1 (S102 in FIG. 11). This S102 corresponds to an example of a calculation step.

Naturally, no administration date is recorded for the injection site of the first injection, so in this case, the number of elapsed days is set to 100 days, for example, to be greater than the administration interval (such as five days). Consequently, enough days have passed for this injection site, making it suitable for injection.

Next, the determination component 102 calculate the display stage of an item from the administration interval and the number of elapsed days (S103 in FIG. 11). This S103 corresponds to an example of a determination step.

For instance, if the administration interval is five days, and the number of elapsed days is one day, (the day after the injection), the number of days until the next injection is four, so the display stage is determined to be 1 (seeds). If the number of elapsed days is two (two days after injection), there are three days left until the next injection, and the display stage is determined to be 2 (sprout). If the number of elapsed days is three, there are two days left until the next injection, and the display stage is determined to be 3 (seedling). If the number of elapsed days is four, there is one day left until the next injection, and the display stage is determined to be 4 (flowers).

If the number of elapsed days is five or more, enough days have passed since the administration date, so injection can be performed at that site. That is, an injection site reaction can be prevented in a state in which problems due to continuous injection are unlikely to occur. The display stage is therefore determined to be 5 (fruit).

The display controller 100 takes the image corresponding to the display stage of the item from the memory 15, and displays this taken image at the location of the site number. For example, the display controller 100 takes an image of an apple from the memory 15, and displays this image of an apple at the injection site P1 as shown in FIG. 5a (S104 in FIG. 11). This S104 corresponds to an example of a display step.

When the above-mentioned processing of S102 to S104 in FIG. 11 is repeated for the injection sites P1 to P6 (S105 in FIG. 11), the various fruits are displayed in their respective growth states at the injection sites P1 to P6. This display guides the patient to the proper injection site (S106 in FIG. 11). That is, either an already-selected display or a selectable display is determined and displayed for each of the injection sites P1 to P6.

In this embodiment, a different item is set for each of the injection sites P1 to P6, and a fruit corresponding to that item is displayed. Therefore, the patient can continue his treatment while enjoying the growth states of various fruits.

The description will now return to S2 in FIG. 10 and continue from there.

In S2 in FIG. 10, if a front/rear switch display operation is performed with the input component 17 when the front side of the body is being displayed as in FIG. 5a, the processing of S101 to S106 in FIG. 11 is performed again. Specifically, this time, as shown in FIG. 5b, the rear of the body is displayed, and fruits are displayed at the injection sites P7 to P10 thereof.

Thus displaying fruits in their harvest state at the injection sites P1 to P10 allows the patient to visually recognize that those injection sites can be selected. The patient can choose a site where injection will be easy for him, from among the sites at which fruits are displayed.

As shown in FIG. 5a, when an injection site is chosen, the display controller 100 causes the display component 6 to display an injection selection icon 18, which is successively moved near the injection sites P1 to P6 according to the selection operation of the input component 17 by the patient. If the injection selection icon 18 is displayed near an "orange," for example, and this is selected with the input component 17, the injection site P4 will be selected (S3 in FIG. 10).

The calculator 101 refers to the information table T1 in FIG. 12, and calculates the number of elapsed days from the administration date at the injection site P4 and the current date on the clock 16 (S4 in FIG. 10).

Next, whether or not the injection site is suitable for injection is determined by the determination component 102 from the number of elapsed days and the administration interval. When a site where a fruit is displayed is selected, the number of elapsed days is greater than the administration interval at the injection site P4, and a sufficient amount of time has passed since the administration date (S5 in FIG. 10), so the display controller 100 displays an injection preparation completion screen (not shown) (S6 in FIG. 10).

After this, the patient injects the pharmaceutical at the injection site P4 he has selected (S7 in FIG. 10).

This injection procedure (pharmaceutical administration procedure) is the same as the conventional procedure, and therefore will not be described in detail here, but when the patient sticks the injection needle 3 into his body and presses the pharmaceutical injection button 5, the controller 14 drives the motor 12 to perform pharmaceutical administration, which moves the piston 9 forward via the gear 11. As a result, the pharmaceutical in the pharmaceutical syringe 8 is administered through the injection needle 3 into the body.

After the pharmaceutical has been administered, the update component 103 updates the item and the administration date in the information table T1 for the site of the current injection (such as the injection site P4). The administration date is updated to today's date, and the item is updated to an item randomly selected from among the fruits A1 to A10 in FIG. 7 (S8 in FIG. 10).

After this, the power button 4 is switched off to conclude the series of injection operations (S9 in FIG. 10).

Then, if another injection is performed on the next day, the above operations in S1 to S11 in FIG. 10 are performed so that a fruit seed (see B1 in FIG. 8) is displayed at the injection site P4 as an already-selected display indicating that this injection site has already been selected, as shown in FIG. 6a.

The patient sees this already-selected display and recognizes that "I can't inject at this site today," and therefore chooses an injection site from among the remaining injection sites P1 to P3 and P5 to P10.

Thus, even if the patient is a child, he can be guided to inject at a different site each time so that the same injection site will not be chosen continuously. As a result, the problems caused by continuous injection at the same site can be eliminated.

The display controller 100 in this embodiment updates the items in the information table T1 after injection, and makes a fruit that is in already-selected display different from a pre-injection (pre-selection) fruit. For instance, a fruit that is in already-selected display is changed from an orange to a melon.

Therefore, the fruit at the injection site is changed after each injection, and the patient can continue treatment while enjoying wondering "Which fruit will it be this time?"

Figure 13:
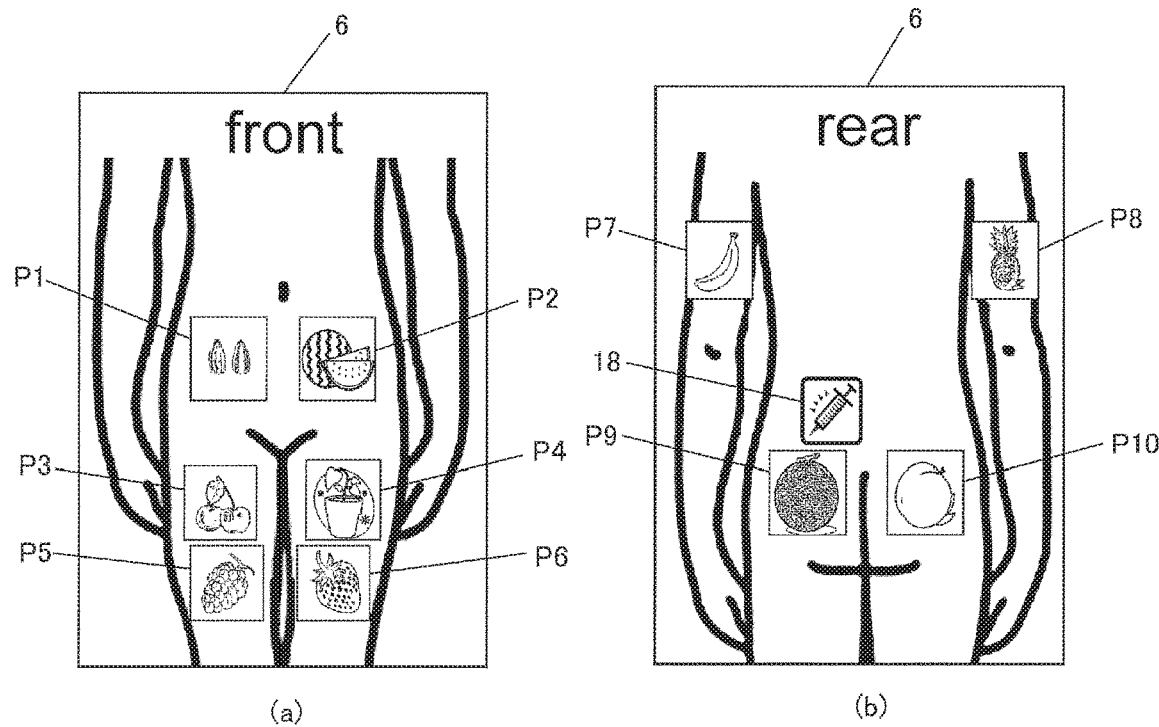
FIGS. 13a and 13b show display examples of the display component pertaining to an embodiment of the present invention.
Figure 14:
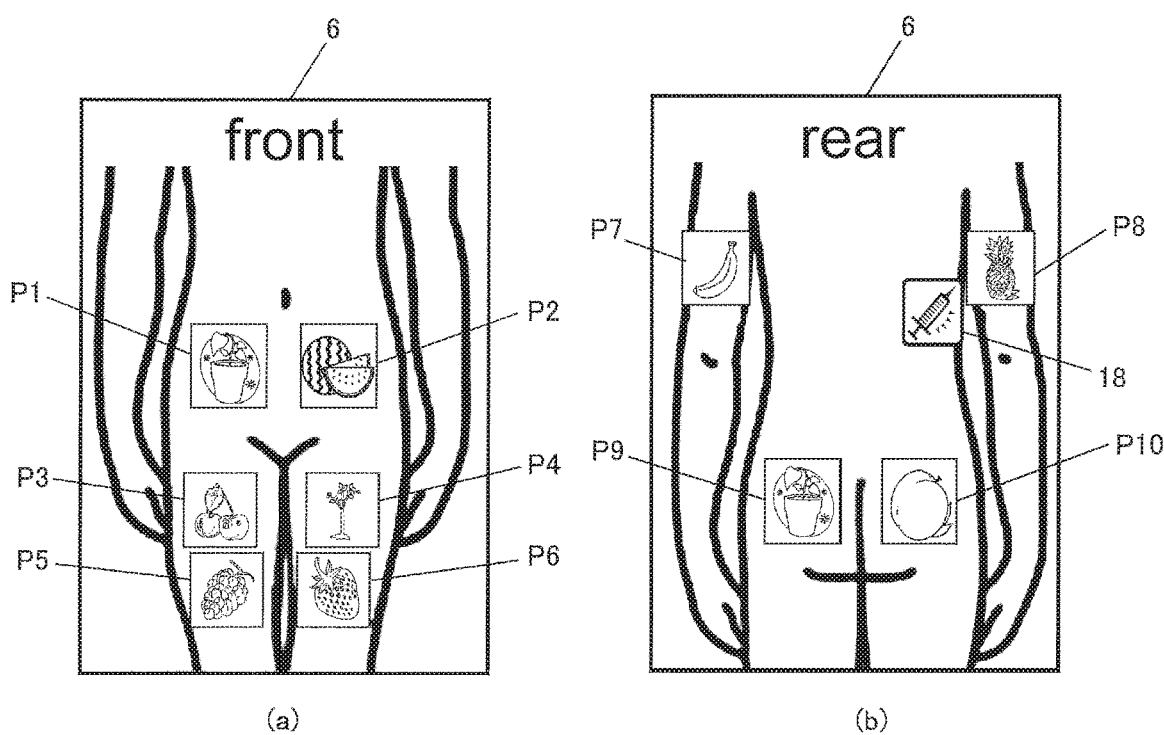
FIGS. 14a and 14b show display examples of the display component pertaining to an embodiment of the present invention.
Figure 15:
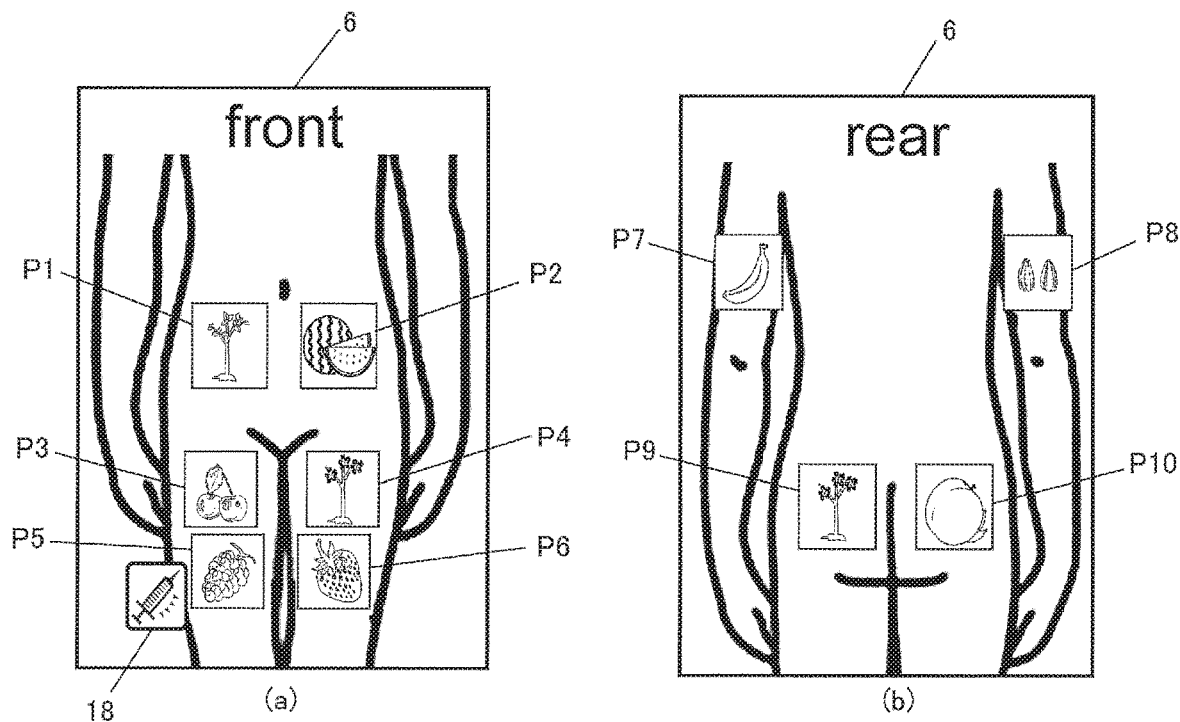
FIGS. 15a and 15b show display examples of the display component pertaining to an embodiment of the present invention.
Figure 16:
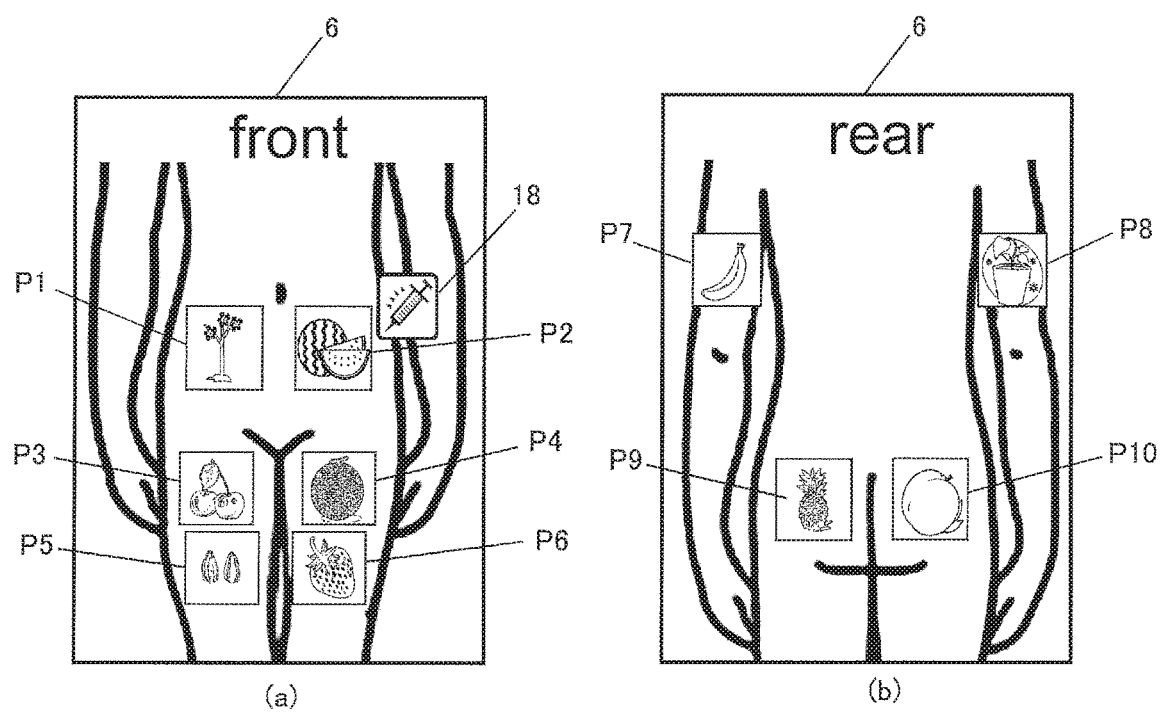
FIGS. 16a and 16b show display examples of the display component pertaining to an embodiment of the present invention.
Figure 17:
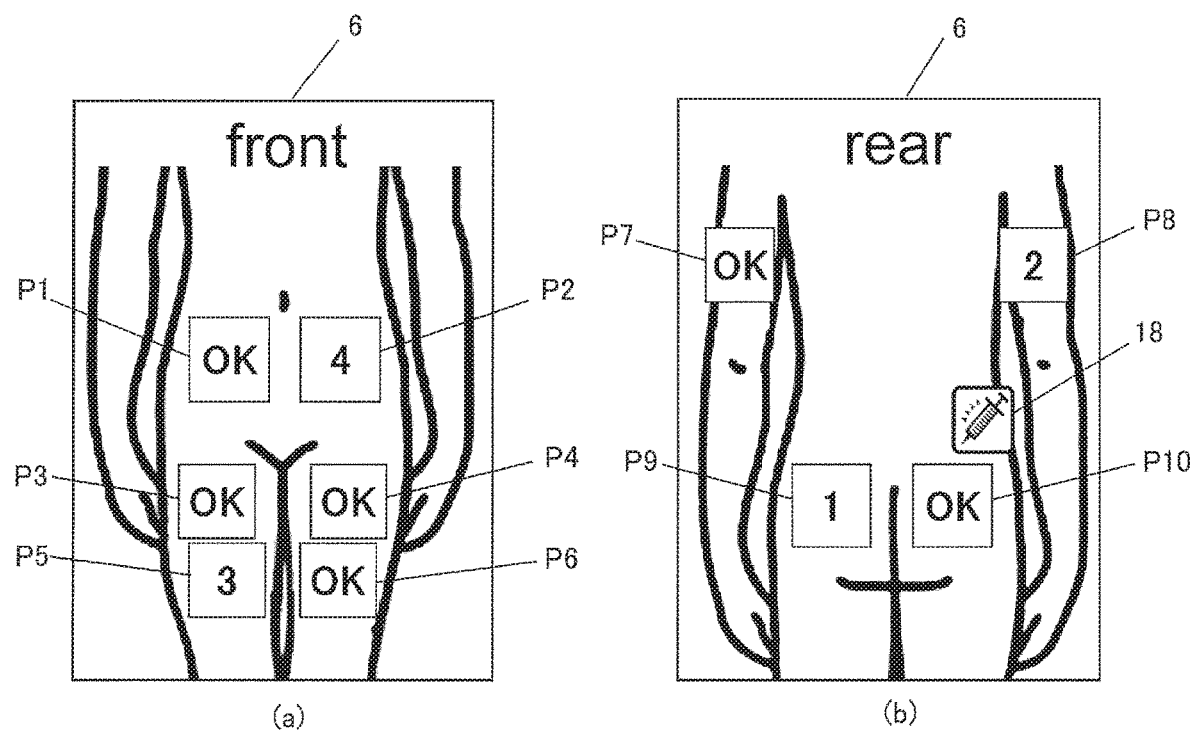
FIGS. 17a and 17b show display examples of the display component pertaining to a modification example of an embodiment of the present invention.

After this, the display of the growth state of the fruit at the injection site P4 is changed daily, first to the sprout in FIG. 13a, then to the seedling in FIG. 14a, and then to the flowers in FIG. 15a. Once the melon (harvest state) is display as in FIG. 16a, this injection site P4 is once again ready for injection.

If a site in already-selected display (a site where seeds, sprout, seedling, or flowers are displayed) is accidentally selected, in S5 in FIG. 10 the determination component 102 compares the number of elapsed days calculated by the calculator 101 to the administration interval, and determines that the number of elapsed days is less than the administration interval. Upon receiving this determination, the display controller 100 causes the display component 6 to display a warning of "The administration interval has not yet passed at this site" (S10 in FIG. 10).

After this, the display controller 100 causes the display component 6 to display "Change injection site?" (S11 in FIG. 10), and if the input component 17 is used to change the injection site, the control goes back to S2 in FIG. 10, and injection site selection is performed again.

There will also be times when a site in already-selected display is intentionally selected. For example, this may happen when an injection site marked with a mature fruit cannot be used for injection because of a wound, etc. In such a case, after the warning display is given in S10 in FIG. 10, a forced injection operation is performed with the input component 17 (S11 in FIG. 10) to move control to S6 in FIG. 10, at which point injection will be possible.

As discussed above, in this embodiment, the patient can be guided to the correct site for injection, so the problems caused by continuous injection at the same site can be eliminated.

Furthermore, the display controller 100 displays three or more injection sites, and displays selectable displays at two or more of these injection sites, from which an injection site can be selected. Accordingly, even if an injection site has become an already-selected display, the patient can always choose the desired injection site from two or more injection sites.

Also, as shown in FIGS. 5a and 5b, the display controller 100 in this embodiment displays selectable displays at all injection sites that are suitable for injection. In FIGS. 5a and 5b, mature fruits are displayed as selectable displays at the injection sites P1 to P10. This allows the patient to visually recognize all of the injection sites that are suitable for injection, which affords the patient a broader range of selection.

In this embodiment, the display component 6 of the portable pharmaceutical injecting device 1, which a patient uses to perform injections by himself, is limited in how many injection sites can be displayed at once, because it is portable. In view of this, a display switching button for displaying other injection sites is provided on the input component 17 in FIG. 4 when there are injection sites that are suitable for injection in addition to the injection sites currently displayed on the display component 6. Therefore, as shown in FIGS. 5, 6, and 13 to 17b, injection sites that are suitable for injection can be displayed while switching between the front and rear displays of the human body diagram, so the patient has more selection options.

Furthermore, in this embodiment, a pharmaceutical administration interval according to a injection site reaction is set for each of the injection sites P1 to P10 displayed on the display component 6, and the number of change days from a seed in a recently planted state (already-selected display) to fruit in a harvest state (selectable display) is set to correspond to this administration interval. Also, the images from seeds to fruits are stored in the memory 15 in a state corresponding to the number of change days.

Therefore, an administration interval is set for each injection site, and the growth state of the fruit corresponding to this administration interval can be displayed. That is, if the pharmaceutical administration interval is five days, the fruit seeds will become a fruit in five days, and if the pharmaceutical administration interval is three days, the fruit seeds will become a fruit in three days.

Moreover, in this embodiment, the display controller 100 causes the display component 6 to display, as the injection sites, two or more of the abdomen, the legs, and the arms, plus the buttocks. The display on the buttocks, assuming that the number of change days from seed to fruit is three days, was less than the number of change days from seed to fruit at the abdomen, the legs, and the arms (five days, for example). That is, since the buttocks are a site where an injection site reaction is unlikely to occur, the number of change days there was set lower than at other sites. This allows the buttocks to revert to selectable status faster than other sites.

3. Features (3-1)

The pharmaceutical injecting device 1 in this embodiment comprises the main body case 2, the piston 9, the drive mechanism 20, the display component 6, and the controller 14. The main body case 2 has the cartridge holder 7 (an example of a pharmaceutical syringe installation component) in which the pharmaceutical syringe 8 is installed. The piston 9 is provided movably with respect to the pharmaceutical syringe 8 installed in the cartridge holder 7. The drive mechanism 20 drives the piston 9. The display component 6 displays the injection sites P1 to P10 at which the pharmaceutical in the pharmaceutical syringe 8 is injected. The display controller 100 displays a plurality of injection sites P1 to P10 on the display component 6, and displays at two or more injection sites selectable displays (A1 to A10) indicating that these injection sites are suitable for injection.

The patient can choose a site where injection will be easy for him each time from among these injection sites in selectable display. Furthermore, the site he has chosen is a site that is suitable for injection, that is, a site where problems caused by continuous injection are unlikely to occur.

Accordingly, even if the patient is a child, he can be guided to inject at a site where injection will be easy for him, and a site where problems caused by continuous injection are unlikely to occur.

As a result, problems caused by continuous injection at the same site can be made less likely to occur.

(3-2)

With the pharmaceutical injecting device 1 in this embodiment, the display controller 100 displays selectable displays at all of the injection sites that are suitable for injection. This allows the patient to select from among more injection sites.

(3-3)

With the pharmaceutical injecting device 1 in this embodiment, the display controller 100 changes a selectable display at one injection site selected after injection (A5 at the injection site P4 in FIG. 5a, for example) to an already-selected display indicating that it is not suitable for injection (B1 at the injection site P4 in FIG. 6a). This allows the patient to easily recognize a site where injection has already been performed.

(3-4)

With the pharmaceutical injecting device 1 in this embodiment, the display controller 100 gives a display indicating when a selected injection site will next become selectable, as an already-selected display.

Here, as an example of a display that indicates when this will happen, the display of B1 to B4 in FIG. 8 is performed, for instance. When the seeds of B1 are displayed, for example, the patient can recognize that an injection was just made at this site, and when the flowers of B4 are displayed, the patient can recognize that the site will soon be ready for injection.

(3-5)

With the pharmaceutical injecting device 1 in this embodiment, the display controller 100 displays, as an already-selected display, the growth state of an article displayed at the selected injection site so as to indicate when this selected injection site will next become selectable. Displaying B1 to B4 in FIG. 8 in this embodiment allows the patient to easily recognize when a site is ready for injection.

(3-6)

With the pharmaceutical injecting device 1 in this embodiment, the display controller 100 displays fruits at each of the injection sites P1 to P10, shows the fruit at an injection site where injection has already been performed in a recently planted state, and changes the display from a recently planted state to a harvest state on the basis of the number of elapsed days since the selection date.

A display such as this makes it easy for even a child to confirm the injection site, and to give injections while enjoying the growth process of the fruits.

(3-7)

With the pharmaceutical injecting device 1 in this embodiment, the display controller 100 displays a different fruit for each of the injection sites P1 to P10. This makes it easy for the patient to identify the injection sites. Also, the patient can continue his treatment while enjoying the growth states of the various fruits.

(3-8)

With the pharmaceutical injecting device 1 in this embodiment, the display controller 100 makes the fruits in already-selected display different from the fruits that have yet to be selected. This means that since the patient does not know which fruits (A1 to A10) will be displayed via the images B1 to B4, he can make his daily injections while enjoying the growth of the fruits.

(3-9)

With the pharmaceutical injecting device 1 in this embodiment, the number of change days from an already-selected display until a selectable display is set for each of the injection sites P1 to P10 displayed on the display component 6. This allows the number of change days to be set lower for sites where an injection site reaction is unlikely to occur than for other sites.

(3-10)

With the pharmaceutical injecting device 1 in this embodiment, the display controller 100 causes the display component 6 to display, as the injection sites, two or more sites on the abdomen, the legs, and the arms, plus the buttocks, and the number of change days at the buttocks is set to be lower than the number of change days at the abdomen, the legs, and the arms.

Since the buttocks are a site where an injection site reaction is unlikely to occur, the number of change days there is set lower than at other sites, and this allows the buttocks to revert to selectable status faster than other sites.

(3-11)

The pharmaceutical injecting device 1 in this embodiment has the determination component 102. The determination component 102 determines whether or not each of the plurality of injection sites P1 to P10 is a site that is suitable for injection. The display controller 100 gives selectable displays (A1 to A10 in FIG. 7) for the injection sites (P1 to P10) determined by the determination component 102 to be suitable for injection.

Consequently, the patient can choose a site each time that affords easy injection from among the injection sites displayed in selectable form. Furthermore, the site the patient chooses will be an injection site that is suitable for injection, that is, one at which continuous injection is unlikely to pose a problem.

(3-12)

With the pharmaceutical injecting device 1 in this embodiment, the display controller 100 displays already-selected displays (B1 to B4 in FIG. 8) indicating that a site is not suitable for injection at the injection sites determined by the determination component 102 to be sites not suitable for injection. This allows already-selected displays and selectable displays to be given.

(3-13)

The pharmaceutical injecting device 1 in this embodiment comprises the memory 15, the update component 103, and the calculator 101. The memory 15 stores information related to the pharmaceutical administration date on which an injection site was selected and injection performed, for each of the plurality of injection sites (P1 to P10). The update component 103 updates information related to the pharmaceutical administration date at one selected injection site after injection. The calculator 101 calculates the elapsed time since the pharmaceutical administration date. The determination component 102 determines whether or not an injection site is suitable for injection on the basis of the elapsed time since the pharmaceutical administration date for each of the injection sites.

Consequently, whether or not an injection site is suitable for injection can be determined from the elapsed time since the pharmaceutical administration date, so the incidence of injection site reaction can be reduced.

(3-14)

With the pharmaceutical injecting device 1 in this embodiment, the pharmaceutical administration interval set for each of the injection sites P1 to P10 is stored in the memory 15 as shown in FIG. 12. The determination component 102 compares the administration interval to the elapsed time since the pharmaceutical administration date, determines that an injection site is suitable for injection if the elapsed time is greater than or equal to the administration interval, and determines that an injection site is not suitable for injection if the elapsed time is less than the administration interval. Consequently, whether or not an injection site is suitable for injection can be determined from the elapsed time since the pharmaceutical administration date on the basis of the administration interval set ahead of time by a doctor or the like, so the incidence of injection site reaction can be reduced.

(3-15)

The display control method for the pharmaceutical injecting device 1 in this embodiment is a method for controlling the pharmaceutical injecting device 1 comprising the main body case 2, the piston 9, the drive mechanism 20, and the display component 6, wherein said method comprises a step S104 (an example of a display step). The main body case 2 has the cartridge holder 7 (an example of a pharmaceutical syringe installation component) in which the pharmaceutical syringe 8 is installed. The piston 9 is provided movably with respect to the pharmaceutical syringe 8 installed in the cartridge holder 7. The drive mechanism 20 drives the piston 9. The display component 6 displays the injection sites P1 to P10 at which the pharmaceutical in the pharmaceutical syringe 8 is injected. S104 (an example of a display step) involves displaying a plurality of the injection sites P1 to P10 on the display component 6, and displaying selectable displays indicating that an injection site is suitable for injection at two or more injection sites.

Other Embodiments (A)

In this embodiment, the already-selected display is such that a fruit growth display is used to show when a selected injection site would next be available for selection, but this is not the only option, and a growth display of a flower or a similar article, or an assembly display of a robot or a similar article may be used instead.

(A-1)

For example, when flowers are used for a growth display, the display controller 100 may display a flower for each of the injection sites (such as P1 to P10), change the flower display at an injection site that has already been selected to a recently planted state, and change from a recently planted state to a full bloom state on the basis of how many days have passed since this selection date.

Naturally, the display controller 100 displays a different flower for each injection site. Furthermore, the display controller 100 may make a flower in already-selected display different from a flower that has yet to be selected.

(A-2)

When robots are used, the display controller 100 may display the process of assembling the robot from feet to head, up to the finished product, on the basis of the number of elapsed days.

(A-3)

As shown in FIGS. 17*a* and 17*b*, the display controller 100 may also display, as the already-selected display, the number of days remaining until injection will be possible, to show when a selected injection site will next become selectable. In this case, the patient can recognize with numerical values the number of remaining days until the date when injection becomes possible.

(A-4)

Figure 18:
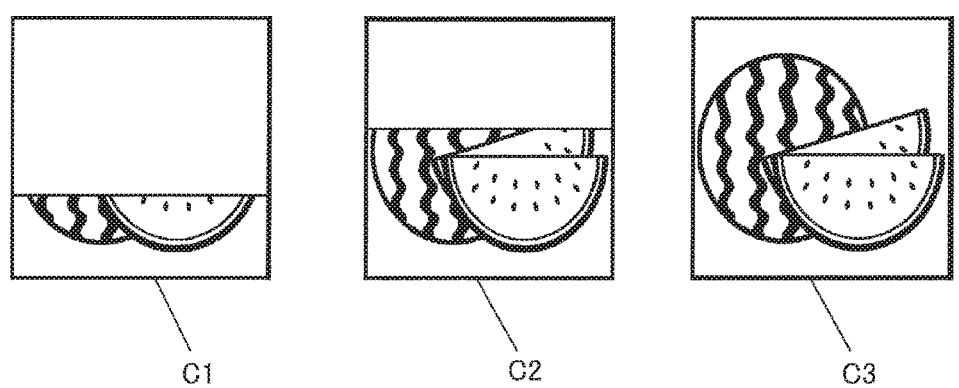
FIG. 18 shows display examples of the display component pertaining to a modification example of an embodiment of the present invention.

Alternatively, as shown by the images C1 to C3 in FIG. 18, the configuration may be such that an article displayed as a selectable display is divided up to show when this selected injection site will next become selectable. In FIG. 18, a watermelon has been divided into three even pieces, and is displayed so that it takes three days to complete the image. With this configuration, injection becomes possible at that injection site when the image is complete.

(B)

In the above embodiment, the information table T1 is stored in the memory 15, but a pharmaceutical administration history may also be stored.

After an injection operation has been performed by using the drive mechanism 20 to move the piston 9, the update component 103 may store the current pharmaceutical administration date and site information indicating the selected injection site in the memory 15. More specifically, the administration history table R1 shown in FIG. 19 is stored in the memory 15, and the update component 103 additionally stores the current pharmaceutical administration date and pharmaceutical administration information about the injection site in this administration history table R1.

Specifically, after the pharmaceutical has been administered in S7 in FIG. 10, the information table T1 is updated in S8 in FIG. 10. At this point, as shown in the administration history table R1 in FIG. 19, the update component 103 (an example of a history update component) additionally stores, as the current pharmaceutical administration information, a history number, the pharmaceutical administration date, the pharmaceutical dose, a site number indicating the selected injection site (an example of site information), the name of this site (an example of site information), an administration interval record, and the item for the injection site selected this time, at the very end of this administration history table R1.

The administration interval record shows the pharmaceutical administration interval for each injection site in number of days, and the calculator 101 compares the current pharmaceutical administration date at the currently selected injection site to the previous pharmaceutical administration date, and makes a calculation.

For example, when the history number "9" is stored in the administration history table R1, the calculator 101 searches the administration history table R1 for the previous administration information corresponding to the site number "1" which is the currently selected injection site. The site number "1" is stored under the history number "2." In view of this, the calculator 101 compares the current administration date to the previous administration date (the administration date of history number "2"), calculates a pharmaceutical administration interval of seven days, and stores 7 as the administration interval in the history number "9."

After a series of injection operations is finished in S9 in FIG. 10, when the power is turned back on and the administration history table R1 is displayed on the display component 6, the number of administrations at each injection site can be seen. As a result, the patient and doctor can set up an administration plan, such as "Let's increase administration at this site."

(C)

In the above embodiment, the injection sites are displayed on the display component 6 of the pharmaceutical injecting device 1, but an injection site display device may be provided apart from the pharmaceutical injecting device. This injection site display device comprises a display component and a display controller. The display controller causes the display component to display a plurality of injection sites, and to display at two or more of the injection sites selectable displays indicating that those injection sites are suitable for injection.

(D)

In the above embodiment, the administration interval varies with the injection site as shown in FIG. 12, but the interval may instead be constant.

(E)

In the above embodiment, the display controller 100, the calculator 101, and the determination component 102 each take out information from the memory 15, but an information takeout component may be provided separately, and information may be transmitted from this information takeout component to the display controller 100, the calculator 101, and the determination component 102. The update component 103 may also serve as an information takeout component for taking out information from the memory 15.

As described above, the display controller 100 in this embodiment causes the display component 6 to display a plurality of injection sites, and to display at two or more of the sites selectable displays indicating that those injection sites are suitable for injection.

Accordingly, since selectable displays are displayed at two or more injection sites, the patient can choose a site where injection will be easy for him, from among the injection sites in selectable display. Furthermore, the site he has chosen will be an injection site that is suitable for injection, that is, at a site at which problems due to continuous injection will be unlikely to occur.

Therefore, even if the patient is a child, he can inject at a site where injection is easy for him, and can be guided to inject at a site where continuous injection is unlikely to pose a problem.

As a result, problems caused by continuous injection at the same site are less likely to occur.

INDUSTRIAL APPLICABILITY

Certain implementations of the pharmaceutical injecting device, method for controlling a pharmaceutical injecting device, and injection site display device of the present invention have the effect of making it less likely that problems due to continuous injection will occur, and are expected to find use as a pharmaceutical injecting device that injects a pharmaceutical such as insulin or a growth hormone.

The invention claimed is:

1. A pharmaceutical injecting device, comprising:
a main body case having a pharmaceutical syringe installation component in which a pharmaceutical syringe is installed;
a piston that is provided movably with respect to the pharmaceutical syringe installed in the pharmaceutical syringe installation component;
a drive mechanism that drives the piston;
a display component that displays injection sites at which a pharmaceutical in the pharmaceutical syringe is injected; and
a display controller that causes the display component to display a plurality of the injection sites and to display, at two or more injection sites, selectable displays, respectively, indicating that the two or more injection sites are suitable for injection,
wherein, after injection, the display controller changes the selectable displays of one selected injection site of the two or more injection sites to an already-selected display indicating unsuitability for injection, and
wherein the display controller displays an article on the already-selected display at the one selected injection site of the two or more injection sites and displays an indication of a growth state of the article displayed at the one selected injection site of the two or more injection sites as an indicator as to when the one selected injection site of the two or more injection sites will again become selectable.

2. The pharmaceutical injecting device according to claim 1, wherein the display controller displays, as the article, a fruit at each of the plurality of injection sites, displays the fruit as a recently-planted-state fruit at an injection site that has been selected on a selection date, and changes the display from the recently-planted-state fruit to a harvest state fruit based on how many days have passed since the selection date.

3. The pharmaceutical injecting device according to claim 2, wherein the display controller displays a different fruit for each of the plurality of injection sites.

4. The pharmaceutical injecting device according to claim 2, wherein the display controller makes the fruit in the already-selected display be different in appearance from a fruit in a display prior to selection.

5. The pharmaceutical injecting device according to claim 1, wherein the display controller displays, as the article, a flower at each of the plurality of injection sites, displays the flower as a recently-planted-state flower at an injection site that has been selected on a selection date, and changes the display from the recently-planted-state flower to a full bloom state flower based how many days have passed since the selection date.

6. The pharmaceutical injecting device according to claim 5, wherein the display controller displays a different flower for each of the plurality of injection sites.

7. The pharmaceutical injecting device according to claim 5, wherein the display controller makes the flower in the already-selected display be different in appearance from a flower in a display prior to selection.

8. The pharmaceutical injecting device according to claim 1, wherein, at the already-selected display, the display controller displays a number of days remaining until injection can be performed, so as to indicate when the already-selected display will next be selectable.

9. The pharmaceutical injecting device according to claim 1, wherein, at the already-selected display, the display controller displays one or more pieces of the article, a number of the pieces indicating when the already-selected display will next be selectable.

10. The pharmaceutical injecting device according to claim 1, wherein a number of change days from the already-selected display to the selectable display is set for each injection site of the plurality of injection sites displayed on the display component.

11. The pharmaceutical injecting device according to claim 10, wherein the display controller causes the display component to display that two or more injection sites are in an abdomen, legs, arms, and the buttocks, wherein a number of days between two consecutive injections at the buttocks is less than a number of days between two consecutive injections at the abdomen, the legs, and the arms.

12. The pharmaceutical injecting device according to claim 1, further comprising:
    a memory for storing site information indicating the plurality of the injection sites, and a date on which pharmaceutical was administered at each injection site of the plurality of injection sites; and
    a history update component for storing in the memory a current pharmaceutical administration date and site information indicating the selected injection site, after the drive mechanism has moved the piston.

13. The pharmaceutical injecting device according to claim 12, further comprising a calculator that calculates pharmaceutical administration interval results from the current pharmaceutical administration date and a last pharmaceutical administration date at the selected injection site,
    wherein the history update component stores the calculated administration interval results in the memory.

14. The pharmaceutical injecting device according to claim 1, further comprising a determination component that determines whether or not each of the plurality of injection sites is a site suitable for injection,
    wherein the display controller displays the selectable display at the injection sites determined by the determination component to be suitable for injection.

15. The pharmaceutical injecting device according to claim 14,
    wherein the display controller displays the already-selected display indicating unsuitability for injection at the injection sites determined by the determination component to be unsuitable for injection.

16. The pharmaceutical injecting device according to claim 15, further comprising:
    a memory for storing information related to a pharmaceutical administration date on which an injection site was selected and injection was performed, for each of the plurality of injection sites;
    an update component that updates information related to the pharmaceutical administration date at one selected injection site after injection; and
    a calculator that calculates an elapsed time since the pharmaceutical administration date,
    wherein the determination component determines whether or not an injection site is suitable for injection, based on the elapsed time, for each of the injection sites.

17. The pharmaceutical injecting device according to claim 16, wherein a pharmaceutical administration interval set for each of the injection sites is stored in the memory,
    the determination component compares the administration interval to the elapsed time,
    if the elapsed time is greater than or equal to the administration interval, the injection site is determined to be a site that is suitable for injection, and
    if the elapsed time is less than the administration interval, the injection site is determined to be a site that is unsuitable for injection.

18. A display control method for a pharmaceutical injecting device that comprises: a main body case having a pharmaceutical syringe installation component in which a pharmaceutical syringe is installed; a piston that is provided movably with respect to the pharmaceutical syringe installed in the pharmaceutical syringe installation component; a drive mechanism that drives the piston; and a display component that displays injection sites at which a pharmaceutical in the pharmaceutical syringe is injected, said method comprising, via a display controller:
    causing the display component to display a plurality of injection sites, and
    causing the display component to display, at two or more injection sites, selectable displays, respectively, indicating that the two or more injection sites are suitable for injection,
    after injection, changing the selectable displays of one selected injection site of the two or more injection sites to an already-selected display indicating unsuitability for injection, and
    displaying an article on the already-selected display at the one selected injection site of the two or more injection sites and displays an indication of a growth state of the article displayed at the one selected injection site of the two or more injection sites as an indicator as to when the one selected injection site of the two or more injection sites will again become selectable.

* * * * *

UNITED STATES PATENT AND TRADEMARK OFFICE
CERTIFICATE OF CORRECTION

PATENT NO. : 10,596,331 B2  
APPLICATION NO. : 15/119705  
DATED : March 24, 2020  
INVENTOR(S) : Tsuguhiro Kondo Page 1 of 1

It is certified that error appears in the above-identified patent and that said Letters Patent is hereby corrected as shown below:

On the Title Page

On page 2, item (56), Other Publications, Line 3, "Internationanl" should read -- International --.

In the Claims

Column 17, Claim 12, Line 15, "pharmaceutical" should read -- the pharmaceutical --.

Signed and Sealed this  
Nineteenth Day of May, 2020

Andrei Iancu  
*Director of the United States Patent and Trademark Office*